US006770576B2

(12) United States Patent
Cook et al.

(10) Patent No.: US 6,770,576 B2
(45) Date of Patent: Aug. 3, 2004

(54) ABSORBENT STRUCTURES OF CHEMICALLY TREATED CELLULOSE FIBERS

(75) Inventors: Jeffery T. Cook, Germantown, TN (US); Robert Irvin Bell, Collierville, TN (US); Sonja McNeil Fields, Memphis, TN (US); Byron Jerry Lee Huff, Memphis, TN (US); Gerald Hunt Morton, Germantown, TN (US); Howard Leon Schoggen, Southaven, MS (US); David Jay Smith, Germantown, TN (US)

(73) Assignee: BKI Holding Corporation, Wilmington, DE (US)

( * ) Notice: Subject to any disclaimer, the term of this patent is extended or adjusted under 35 U.S.C. 154(b) by 0 days.

(21) Appl. No.: 10/360,147

(22) Filed: Feb. 7, 2003

(65) Prior Publication Data

US 2003/0157857 A1 Aug. 21, 2003

Related U.S. Application Data

(62) Division of application No. 09/469,930, filed on Dec. 21, 1999, now Pat. No. 6,562,743.
(60) Provisional application No. 60/117,565, filed on Jan. 27, 1999, and provisional application No. 60/113,849, filed on Dec. 24, 1998.

(51) Int. Cl.[7] ............................................... B32B 5/02
(52) U.S. Cl. ...................... 442/59; 442/118; 442/119; 442/153; 442/409; 442/417; 442/414; 442/121
(58) Field of Search ......................... 442/59, 118, 119, 442/153, 409, 417, 414, 121

(56) References Cited

U.S. PATENT DOCUMENTS

| 213,100 A | 3/1879 | Eaton |
|---|---|---|
| 1,571,048 A | 1/1926 | Garrow |
| 1,990,292 A | 2/1935 | Leatherman |

(List continued on next page.)

FOREIGN PATENT DOCUMENTS

| CA | 1 193 808 | 9/1985 |
|---|---|---|
| EP | 0 463 388 A1 | 1/1992 |

(List continued on next page.)

OTHER PUBLICATIONS

Buchholz, F. et al., *Modern Superabsorbent Polymer Technology*, pp. 56–58.
Gao, D. et al., *Advances in Cement Research*, 1997, 9:35:93–97.

(List continued on next page.)

*Primary Examiner*—Elizabeth M. Cole
(74) *Attorney, Agent, or Firm*—Darby & Darby

(57) ABSTRACT

Disclosed are absorbent structures including fibers bound with a polyvalent cation-containing compound and superabsorbent polymer particles. The fibers exhibit an ion extraction factor of at least 5%. Also disclosed are multi-strata absorbent structures, such as disposable absorbent articles, including the treated fibers and SAP particles. Further disclosed are methods for preparing absorbent structures including the treated fibers; structures including fibers combined with a polyvalent cation-containing compound; and methods for treating or coating SAP particles with polyvalent cation-containing compounds.

13 Claims, 8 Drawing Sheets

U.S. PATENT DOCUMENTS

| | | |
|---|---|---|
| 2,032,645 A | 3/1936 | Youtz |
| 2,097,589 A | 11/1937 | Dreyfus |
| 2,289,282 A | 7/1942 | Brodersen et al. |
| 2,525,049 A | 10/1950 | Signaigo |
| 2,739,871 A | 3/1956 | Senkus et al. |
| 2,983,722 A | 5/1961 | Horowitz et al. |
| 3,053,607 A | 9/1962 | Gulledge |
| 3,224,926 A | 12/1965 | Bernardin |
| 3,873,354 A | 3/1975 | Walters |
| 3,935,363 A | 1/1976 | Burkholder et al. |
| 3,998,690 A | 12/1976 | Lyness et al. |
| 4,043,952 A | 8/1977 | Ganslaw et al. |
| 4,090,013 A | 5/1978 | Ganslaw et al. |
| 4,102,340 A | 7/1978 | Mesek et al. |
| 4,295,987 A | 10/1981 | Parks |
| 4,302,369 A | 11/1981 | Elmquist |
| 4,306,911 A | 12/1981 | Gordon et al. |
| 4,406,703 A | 9/1983 | Guthrie et al. |
| 4,447,570 A | 5/1984 | Cook et al. |
| 4,467,012 A | 8/1984 | Pedersen et al. |
| 4,469,746 A | 9/1984 | Weisman et al. |
| 4,506,684 A | 3/1985 | Keritsis |
| 4,548,847 A | 10/1985 | Aberson et al. |
| 4,558,091 A | 12/1985 | Hubbard |
| 4,699,823 A | 10/1987 | Kellenberger et al. |
| 4,715,931 A | 12/1987 | Schellhamer et al. |
| RE32,649 E | 4/1988 | Brandt et al. |
| 4,888,238 A | 12/1989 | Katz et al. |
| 4,898,642 A | 2/1990 | Moore et al. |
| 4,919,681 A | 4/1990 | Tyler et al. |
| 4,935,022 A | 6/1990 | Lash et al. |
| 4,950,264 A | 8/1990 | Osborn, III |
| 4,950,265 A | 8/1990 | Taylor |
| 4,952,550 A | 8/1990 | Wallach et al. |
| 5,147,343 A | 9/1992 | Kellenberger |
| 5,149,335 A | 9/1992 | Kellenberger et al. |
| 5,190,563 A | 3/1993 | Herron et al. |
| 5,217,445 A | 6/1993 | Young et al. |
| 5,294,299 A | 3/1994 | Zeuner et al. |
| 5,300,192 A | 4/1994 | Hansen et al. |
| 5,328,935 A | 7/1994 | Van Phan et al. |
| 5,338,766 A | 8/1994 | Phan et al. |
| 5,350,799 A | 9/1994 | Woodrum et al. |
| 5,360,420 A | 11/1994 | Cook et al. |
| 5,372,766 A | 12/1994 | Roe |
| 5,399,591 A | 3/1995 | Smith et al. |
| 5,413,676 A | 5/1995 | Nguyen et al. |
| 5,417,977 A | 5/1995 | Honeycutt |
| 5,427,844 A | 6/1995 | Murai et al. |
| 5,432,000 A | 7/1995 | Young, Sr. et al. |
| 5,451,613 A | 9/1995 | Smith et al. |
| 5,462,972 A | 10/1995 | Smith et al. |
| 5,484,896 A | 1/1996 | Naieni et al. |
| 5,489,469 A | 2/1996 | Kobayashi et al. |
| 5,492,759 A | 2/1996 | Eriksson et al. |
| 5,562,642 A | 10/1996 | Smith et al. |
| 5,562,646 A | 10/1996 | Goldman et al. |
| 5,589,256 A | 12/1996 | Hansen et al. |
| 5,601,921 A | 2/1997 | Eriksson |
| 5,611,890 A | 3/1997 | Vinson et al. |
| 5,721,295 A | 2/1998 | Bruggemann et al. |
| 5,736,595 A | 4/1998 | Gunther et al. |
| 5,773,542 A | 6/1998 | Koudate et al. |
| 5,789,326 A | 8/1998 | Hansen et al. |
| 5,795,439 A | 8/1998 | Euripides et al. |
| 5,795,515 A | 8/1998 | Fischer |
| 5,847,031 A | 12/1998 | Klimmek et al. |
| 5,849,816 A | 12/1998 | Suskind et al. |
| 5,859,077 A | 1/1999 | Reichman et al. |
| 5,961,505 A | 10/1999 | Coe et al. |
| 5,998,695 A | 12/1999 | Roe et al. |
| 6,040,251 A | 3/2000 | Caldwell |
| 6,074,530 A | 6/2000 | Tillirson |
| 6,080,277 A | 6/2000 | Oberkofler et al. |
| 6,099,950 A | 8/2000 | Wang et al. |
| 6,127,593 A | 10/2000 | Bjorkquist et al. |
| 6,159,335 A | 12/2000 | Owens et al. |
| 6,222,091 B1 | 4/2001 | Beihoffer et al. |
| 6,228,217 B1 | 5/2001 | Dickerson et al. |
| 6,235,965 B1 | 5/2001 | Beihoffer et al. |
| 6,296,737 B1 | 10/2001 | Wu et al. |
| 6,340,408 B1 | 1/2002 | Norlander |
| 6,433,058 B1 | 8/2002 | Weir et al. |

FOREIGN PATENT DOCUMENTS

| | | |
|---|---|---|
| EP | 0 644 207 B1 | 3/1995 |
| EP | 733648 | 9/1996 |
| EP | 856528 A1 | 8/1998 |
| EP | 889063 A1 | 7/1999 |
| JP | 7-228788 A | 8/1995 |
| JP | 9-176427 A | 7/1997 |
| JP | 10-489 A | 1/1998 |
| SE | 462 918 | 9/1990 |
| WO | WO 97/39188 | 10/1997 |
| WO | WO 98/17856 | 4/1998 |
| WO | WO 99/55393 | 11/1999 |
| WO | WO 99/55767 | 11/1999 |

OTHER PUBLICATIONS

Herrmann, E., *Edana's 1998 International Nonwovens Symposium*, pp. 5.4–5.16.

J. Grignon et al., "Effect of pH and Neutral Salt upon the Swelling of Cellulose Gels", Journal of Applied Polymer Science, vol. 25, 2829–2843 (1980).

Omidian, H., et al., *Polymer*, 1999, 40:1753–1761.

Shimomura, T., Polymeric Materials Science and Engineering, pp. 485–486.

Trimnell, D. et al., "Wicking and Absorbency in Aluminum and Silicate Modified Starch Graft Copolymer Superabsorbents" pp. 203–211.

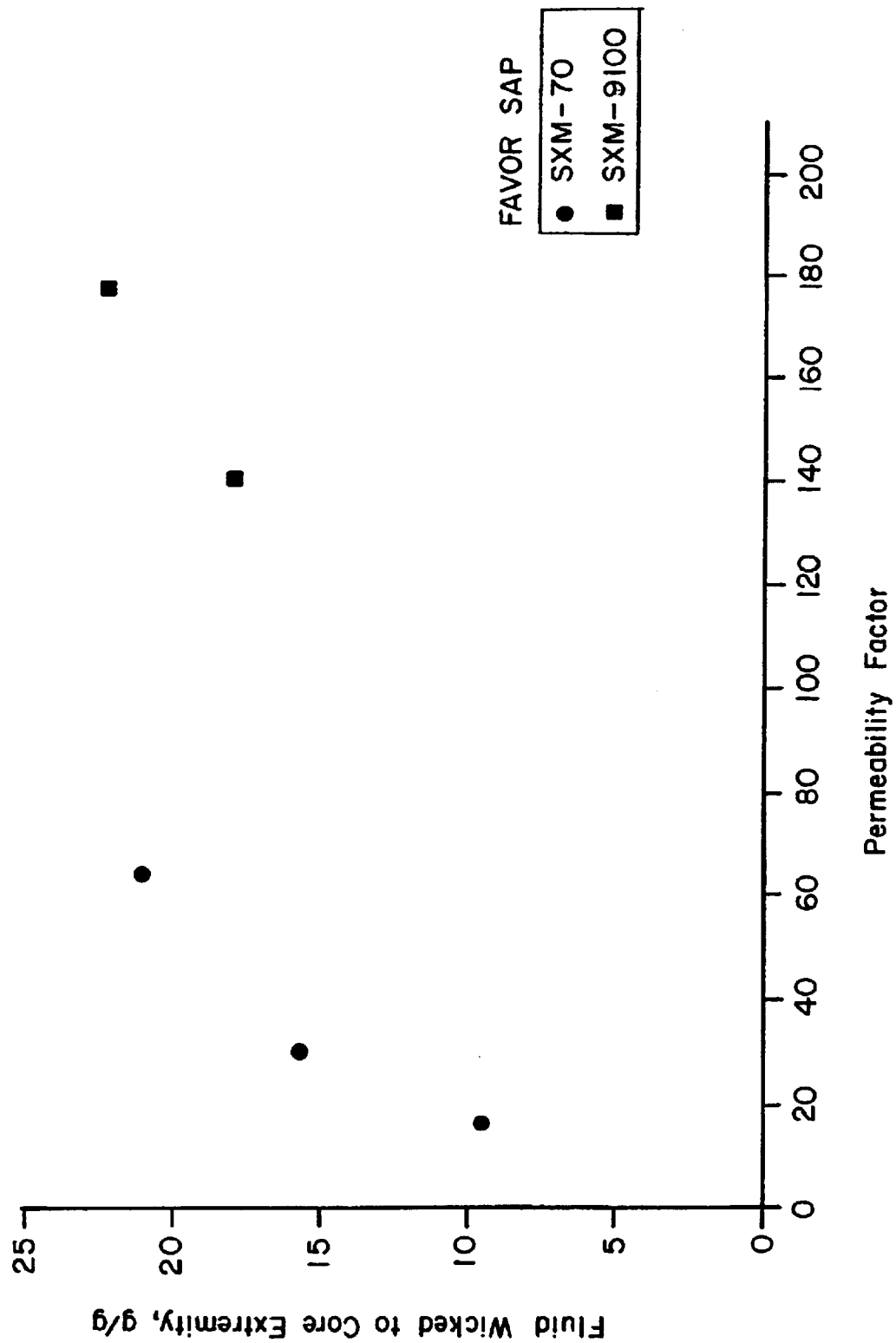

ABSORBENT STRUCTURES OF CHEMICALLY TREATED CELLULOSE FIBERS

CROSS-REFERENCE TO RELATED APPLICATIONS

This is a division of application Ser. No. 09/469,930, filed Dec. 21, 1999, now U.S. Pat. No. 6,562,743, which turn claims the benefit of U.S. Provisional Application Serial No. 60/117,565 filed Jan. 27, 1999, and U.S. Provisional Application Serial No. 60/113,849 filed Dec. 24, 1998. Each of these prior applications is hereby incorporated herein by reference, in its entirety.

FIELD OF THE INVENTION

The present invention relates to a fiber treated to enhance permeability of an absorbent structure prepared from such fibers. More particularly, the invention relates to fibers treated with polyvalent metal ion-containing compounds for use in absorbent structures made with such fibers, and absorbent articles containing such absorbent structures.

BACKGROUND OF THE INVENTION

Absorbent structures are important in a wide range of disposable absorbent articles including infant diapers, adult incontinence products, sanitary napkins and other feminine hygiene products and the like. These and other absorbent articles are generally provided with an absorbent core to receive and retain body liquids. The absorbent core is usually sandwiched between a liquid pervious topsheet, whose function is to allow the passage of fluid to the core and a liquid impervious backsheet whose function is to contain the fluid and to prevent it from passing through the absorbent article to the garment of the wearer of the absorbent article.

An absorbent core for diapers, adult incontinence pads and feminine hygiene articles frequently includes fibrous batts or webs constructed of defiberized, loose, fluffed, hydrophilic, cellulosic fibers. Such fibrous batts form a matrix capable of absorbing and retaining some liquid. However, their ability to do so is limited. Thus, superabsorbent polymer ("SAP") particles, granules, flakes or fibers (collectively "particles"), capable of absorbing many times their weight of liquid, are often included in the absorbent core to increase the absorbent capacity of the core, without having to substantially increase the bulkiness of the core. In an absorbent core containing matrix fibers and SAP particles, the fibers physically separate the SAP particles, provide structural integrity for the absorbent core, and provide avenues for the passage of fluid through the core.

Absorbent cores containing SAP particles have been successful, and in recent years, market demand has increased for thinner, more absorbent and more comfortable absorbent articles. Such an article may be obtained by increasing the proportion of SAP particles to the cellulose or other matrix fibers in the absorbent core.

However, there are practical limits to increasing the proportion of SAP particles in the absorbent core. If the concentration of SAP particles in an absorbent core is too high, gel blocking can result. When SAP particles distributed through an absorbent core of matrix fibers are exposed to liquid they swell as they absorb the liquid, forming a gel. As adjacent SAP particles swell, they form a barrier to free liquid not immediately absorbed by the SAP particles. As a result, access by the liquid to unexposed SAP particles may be blocked by the swollen (gelled) SAP particles. When gel blocking occurs, liquid pooling, as opposed to absorption, takes place in the core. As a result, large portions of the core remain unused, and failure (leaking) of the absorbent core can occur. Gel blocking caused by high concentrations of SAP particles results in reduced core permeability, or fluid flow, under pressures encountered during use of the absorbent product.

One way to minimize gel block (and maintain core permeability) is to limit the proportion of SAP particles to matrix fibers in the absorbent core. In this way, there is sufficient separation between particles, such that even after the particles have been swollen by exposure to liquid they do not contact adjacent particles and free liquid can migrate to unexposed SAP particles. Unfortunately, limiting the concentration of SAP particles in the absorbent core also limits the extent to which the core can be made thinner and more comfortable. To avoid gel block, commercial absorbent cores are presently limited to SAP particle concentrations of 20% to 50% by weight of the core.

It would be highly desirable to provide an absorbent core capable of bearing a SAP particle concentration exceeding 50% by weight, preferably 50% to 80% by weight, while maintaining core permeability and avoiding the problem of gel block. It would also be desirable to provide an absorbent core, which exhibits improved permeability for a given SAP concentration. At the same time, it is important to be able to blend the matrix fiber and SAP particles into an absorbent core using conventional material shipping and handling processes to provide attractive economics for the manufacture of infant diapers, feminine hygiene pads, adult incontinence pads, and the like.

Other methods for increasing SAP particle concentrations while minimizing gel block, have been directed to modifying the superabsorbent polymer itself. Modification of the superabsorbent polymer usually involves reducing the gel volume of the superabsorbent polymer particles by increasing the crosslinking of the polymer. A crosslinked SAP particle is restricted in its ability to swell, and therefore has a reduced capacity, or gel volume. Although modified SAP particles are less susceptible to gel block, they also absorb less liquid by weight due to their reduced gel volume. Modified SAP particles also tend to be brittle and fracture and crack during or after processing into the final absorbent product. A variety of crosslinkers are known in the art. It is also known to use polyvalent metal ions, including aluminum, during the manufacture of SAPs, to serve as an ionic crosslinking agent. See for example, U.S. Pat. No. 5,736,595.

Crosslinking of SAP particles affects the permeability of the particle, i.e., the ability of liquid to permeate the particle to the center, thereby fully utilizing the capacity of the SAP particle. As used in this specification, SAP particle permeability is distinguished from the permeability of the "core" or absorbent structure. Core permeability refers to the ability of liquid to permeate through an absorbent structure containing SAP particles. As used herein, such permeability is measured by methods including "vertical" permeability and "inclined" permeability. A core "permeability factor" may be determined from both vertical and inclined permeability measurements.

A method for improved utilization of the superabsorber is disclosed in U.S. Pat. No. 5,147,343, where particle size distribution of the granules is controlled. By controlling the particle size of the superabsorber and hence the surface area, the rate of fluid uptake can be optimized to the core design.

However, the utilization of the absorbent core is reduced at higher concentrations of SAP particles due to gel blocking.

SUMMARY OF THE INVENTION

The present invention is directed to absorbent structures including fibers bound with a polyvalent cation-containing compound and superabsorbent polymer particles. The fibers exhibit an ion extraction factor of at least 5%. The present invention is also directed to multi-strata absorbent structures, such as disposable absorbent articles, including the treated fibers and SAP particles.

The present invention is also directed to methods for preparing absorbent structures including the treated fibers; structures including fibers combined with a polyvalent cation-containing compound; and methods for treating or coating SAP particles with polyvalent cation-containing compounds.

BRIEF DESCRIPTION OF THE DRAWINGS

FIG. 8 is a graph illustrating the relationship between permeability factor and absorbent structure performance, as measured by fluid wicked to structure extremity, for absorbent structures prepared according to the present invention.

DETAILED DESCRIPTION OF THE PREFERRED EMBODIMENTS

All patents, patent applications, and publications cited in this specification are hereby incorporated by reference in their entirety. In case of conflict in terminology, the present disclosure controls.

It has now been surprisingly and unexpectedly discovered that by treating fibers with a polyvalent ion-containing compound, an absorbent structure (or core) made from such fibers and SAP particles exhibits reduced gel blocking and increased core permeability. As a result, the concentration of SAP particles in an absorbent core may be increased without experiencing gel block or loss in permeability of the core. This allows for better utilization of the absorbent core, because a high fluid flow can be maintained under usage pressure in the absorbent core, thus enabling manufacturers to produce thinner, more absorbent and more comfortable absorbent structures.

Figure 7:
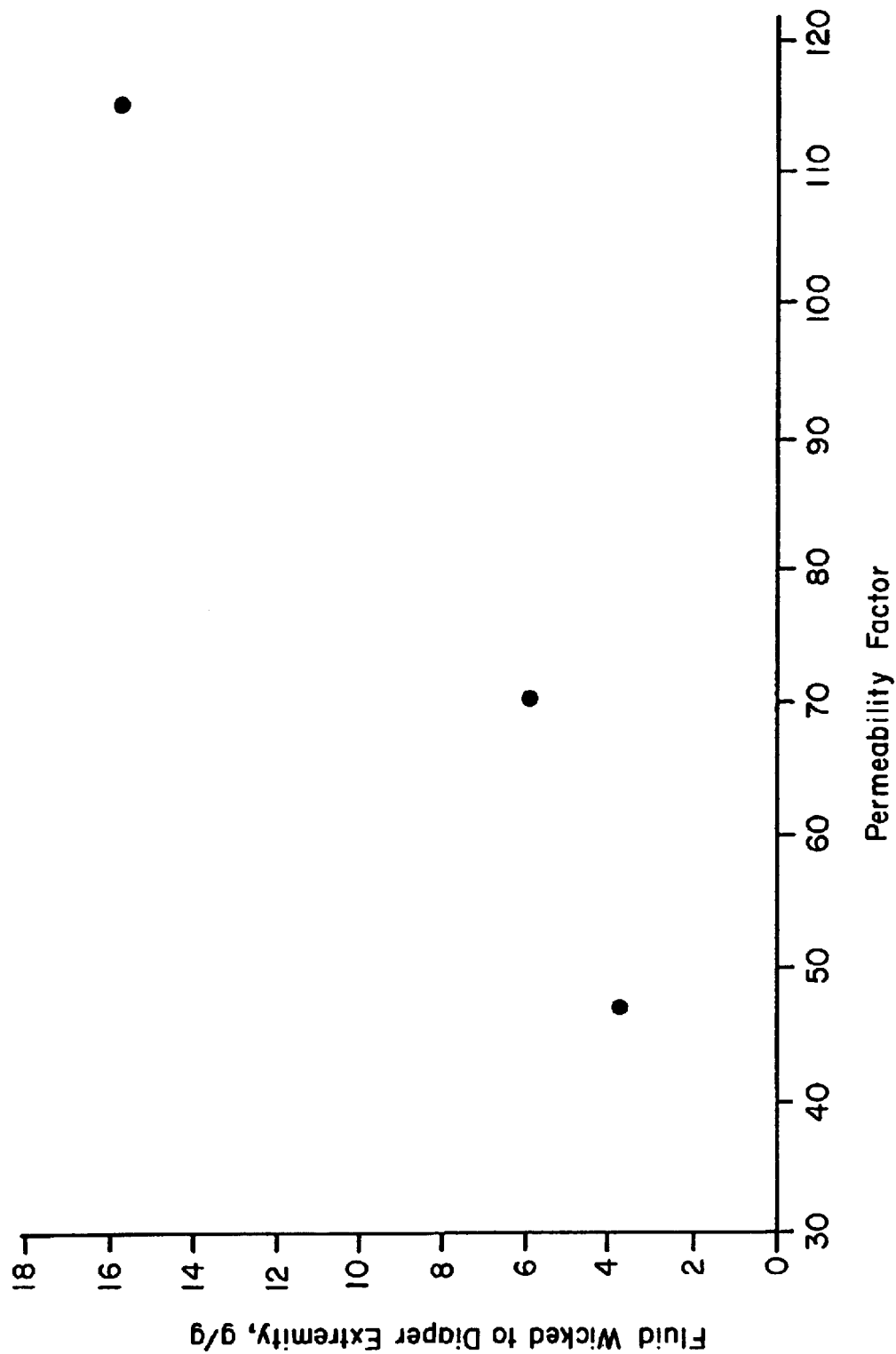
FIG. 7 is a graph illustrating the relationship between permeability factor and disposable diaper performance as measured by fluid wicked to diaper extremity, for absorbent structures prepared according to the present invention.

FIG. 8 exemplifies the improvement in absorbent cores as the permeability is increased. In the figure, the fluid wicked to the core extremity refers to the last three inches of the core material as measured by the horizontal wicking test as described in the procedures section. For two types of SAP, an improvement in core utilization is noted. Further, FIG. 7 shows that for machine-made diapers, the permeability improvement also provides an improvement in core utilization as measured by the horizontal wicking test.

When an absorbent core made with SAP particles and fibers treated with a polyvalent metal-ion containing compound according to the present invention is exposed to liquid, the polyvalent metal ion is released from the fibers, carried by the liquid and contacts the surface of the SAP particle. The polyvalent metal ion inhibits the rate of swelling of the SAP particle sufficiently to enable liquid to permeate beyond the swelling SAP particles to contact unexposed SAP particles. Although the rate of swelling is reduced, the extent of swelling of the SAP particles is not significantly affected by contact with liquid containing the polyvalent metal ion.

Figure 6:
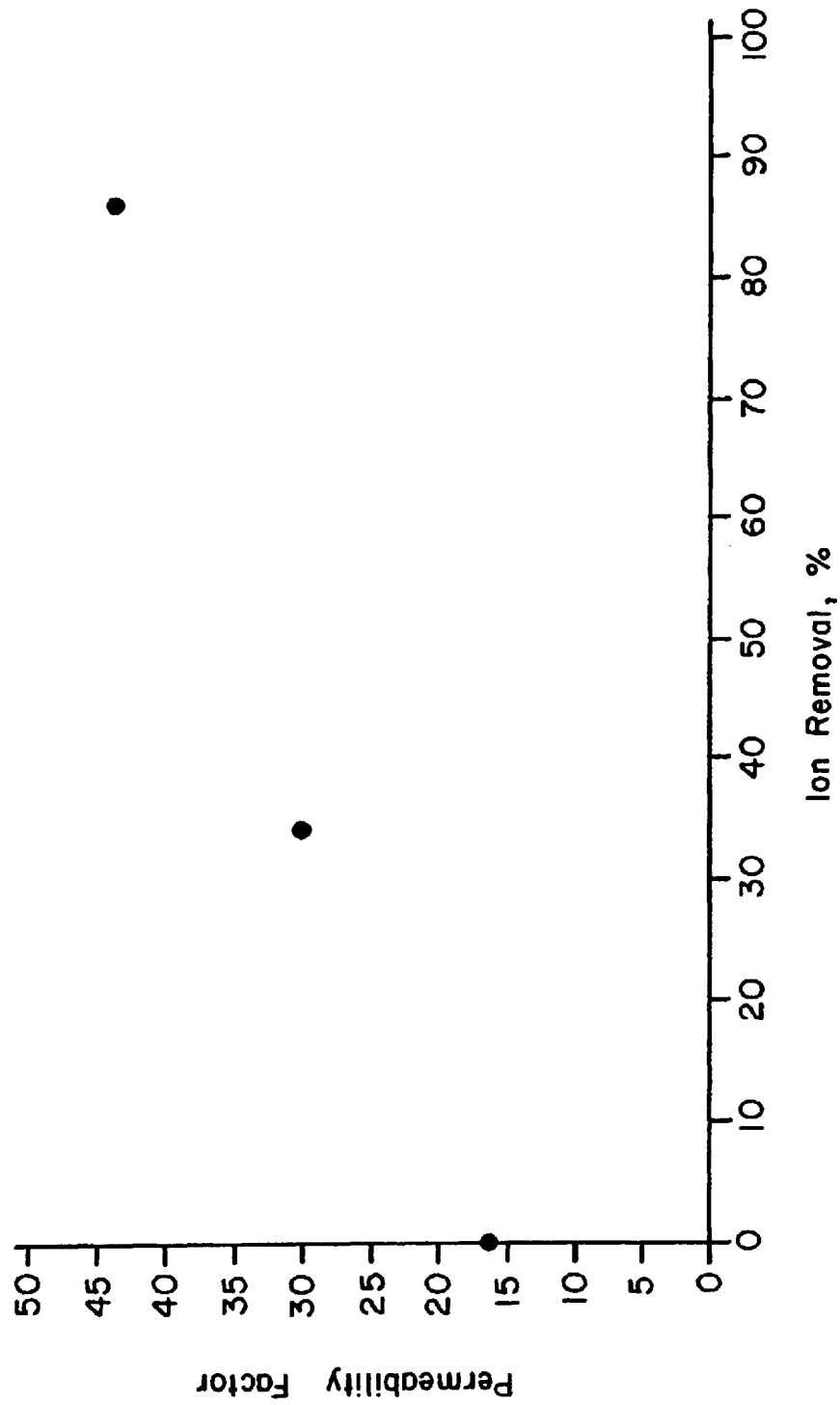
FIG. 6 is a graph illustrating the relationship between permeability factor and ion removal, for absorbent structures prepared according to the present invention.

To prepare fibers suitable for use in an absorbent core, any compatible polyvalent metal ion-containing compound may be employed, provided that the compound releases the polyvalent metal ion upon exposure of the treated fiber to the liquid encountered in the core. The degree to which the polyvalent ion is released from the fiber upon exposure to liquid is referred to herein as "ion extraction". The degree of "ion extraction" is related to the permeability of cores as illustrated in FIG. 6. In this figure increasing ion extraction provides increased permeability.

It is not necessary that the compound chemically bond with the fibers, although it is preferred that the compound remain associated in close proximity with the fibers, by coating, adhering, precipitation, or any other mechanism such that it is not dislodged from the fibers during normal handling of the fibers, absorbent core or absorbent article before contact with liquid. For convenience, the association between the fiber and the compound discussed above may be referred to as the "bond," and the compound may be said to be bound to the fiber.

This concept is exemplified as follows: sheeted cellulosic fibers treated with a water insoluble aluminum compound had the same aluminum concentration before and after hammer mill disintegration (Kamas mill). Sheeted cellulosic fibers treated with a water soluble aluminum compound the same aluminum concentration before disintegration (Kamas mill) and after disintegration. Sheeted cellulosic fibers treated with a water insoluble and a water soluble aluminum compound had the same aluminum concentration before disintegration (Kamas mill) and after disintegration.

Any polyvalent metal salt including transition metal salts may be used, provided that the compound is capable of releasing the polyvalent metal ion upon contact with liquid encountered in the absorbent core. The polyvalent metal containing compound selected for this application should be compatible with safe contact with human skin and mucous membranes. Examples of suitable polyvalent metals include beryllium, magnesium, calcium, strontium, barium, titanium, zirconium, vanadium, chromium, molybdenum, tungsten, manganese, iron, cobalt, nickel, copper, zinc, aluminum and tin. Preferred ions include aluminum, iron and tin. The preferred metal ions have oxidation states of +3 or +4. The most preferred ion is aluminum. Any salt containing the polyvalent metal ion may be employed, provided that the compound is capable of releasing the polyvalent metal ion upon contact with liquid encountered in the absorbent core. Examples of suitable inorganic salts of the above metals include chlorides, nitrates, sulfates, borates, bromides, iodides, fluorides, nitrides, perchlorates, phosphates, hydroxides, sulfides, carbonates, bicarbonates, oxides, alkoxides phenoxides, phosphites, and hypophosphites. Examples of suitable organic salts of the above metals include formates, acetates, butyrates, hexanoates, adipates, citrates, lactates, oxalates, propionates, salicylates, glycinates, tartrates, glycolates, sulfonates, phosphonates, glutamates, octanoates, benzoates, gluconates, maleates, succinates, and 4,5-dihydroxy-benzene-1,3-disulfonates. In addition to the polyvalent metal salts, other compounds such as complexes of the above salts include amines, ethylenediaminetetra-acetic acid (EDTA), diethylenetriaminepenta-acetic acid (DTPA), nitrilotri-acetic acid (NTA), 2,4-pentanedione, and ammonia.

Figure 4:
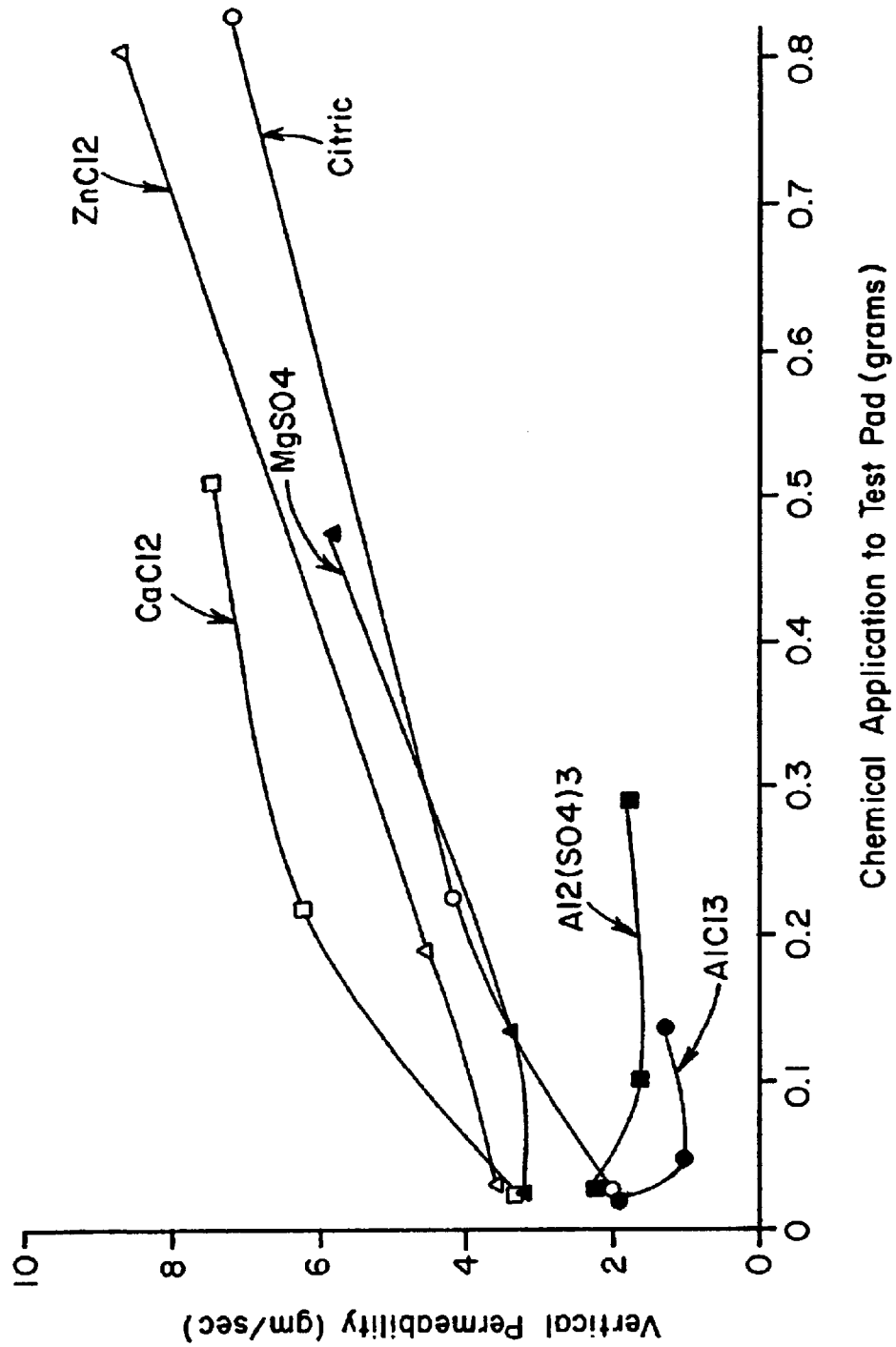
FIG. 4 is a graph illustrating vertical permeability of SAP-containing absorbent structures after application of 0.9% saline solution having various compounds dissolved in the saline at different concentrations.
Figure 5:
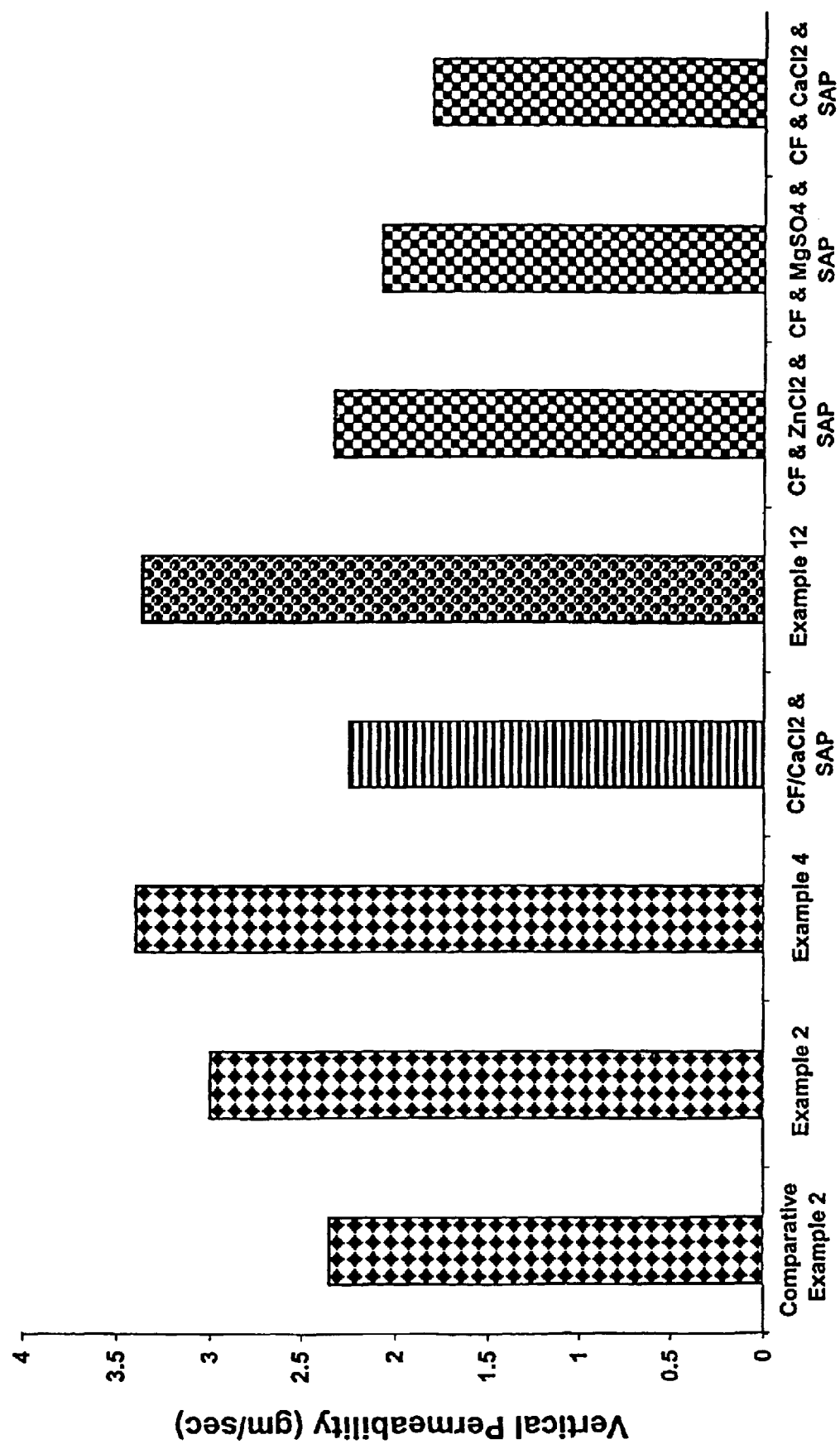
FIG. 5 is a graph illustrating vertical permeability of SAP-containing absorbent structures made with fibers treated with various compounds, or absorbent structures having various compounds applied to thereto.

It has been surprisingly discovered that trivalent aluminum ions are the preferred polyvalent metal ions for minimizing gel block. FIG. 4 shows the effect of a variety of polyvalent metal containing compounds on vertical permeability of test cores containing SAP and cellulose fiber. This data indicates that several polyvalent metal cations produce a higher vertical permeability in the test core than the aluminum salts, when the polyvalent metal containing compounds are dissolved in the mobile phase (0.9% saline) of the vertical permeability test. FIG. 5 shows the effect of a variety of polyvalent metal containing compounds on the vertical permeability test cores containing SAP and cellulose fiber pretreated with the polyvalent metal salt, or test cores that are a mixture of SAP and cellulose fiber and the polyvalent metal salt. This data indicates that the test cores containing the aluminum salts have superior vertical permeability to those containing other polyvalent metal containing compounds. Accordingly, preferred compounds are those which contain aluminum and are capable of releasing aluminum ions upon contact with liquid encountered in the absorbent core. Examples of such compounds include aluminum salts such as aluminum chloride, aluminum sulfate and aluminum hydroxide.

Depending on the polyvalent metal ion containing compound used to treat the fiber, it may be necessary to provide other components, to cause or enhance ionization when liquid contacts the treated fiber. For example, if aluminum hydroxide is employed as the metal ion containing compound, and is precipitated onto the hydrophilic fibers, it is necessary to also treat the fiber with an ionizable acid, for example citric acid. When the treated fiber is exposed to liquid, such as urine for example, the liquid will solubilize the acid, reducing the pH of the liquid and thereby ionizing the aluminum hydroxide to provide aluminum ions in the form of aluminum citrate. A variety of suitable acids may be employed, although the acid preferably should have a low volatility, be highly soluble in water, and bond to the fiber. Examples include inorganic acids such as sodium bisulfate and organic acids such as formic, acetic, aspartic, propionic, butyric, hexanoic, benzoic, gluconic, oxalic, malonic, succinic, glutaric, tartaric, maleic, malic, phthallic, sulfonic, phosphonic, salicylic, glycolic, citric, butanetetracarboxylic acid (BTCA), octanoic, polyacrylic, polysulfonic, polymaleic, and lignosulfonic acids, as well as hydrolyzed-polyacrylamide and CMC (carboxymethylcellulose). Among the carboxylic acids, acids with two carboxyl groups are preferred, and acids with three carboxyl groups are more preferred. Of these acids, citric acid is most preferred.

In general, the amount of acid employed is dictated by the acidity and the molecular weight of that acid. Generally it is found that an acceptable range of acid application is 0.5%–10% by weight of the fibers. As used herein, the "percent by weight," refers to the weight percent of dry fiber treated with the polyvalent metal containing compound. For citric acid the preferred range of application is 0.5%–3% by weight of the fibers.

As discussed above, the treatment of fibers with a polyvalent ion-containing compound increases core permeability. Such treatment results in stiffening of the fibers. The stiffened fibers do not swell in water to the extent that untreated fibers do. Consequently existing interfiber channels or other avenues for liquid to flow through an absorbent structure formed from the fibers are kept open to a greater extent by the stiffened fibers than by the untreated fibers. The reduction in wet swell that is produced by polyvalent ion treatment of the fibers, represents an important contribution to the overall improved permeability of an absorbent core containing SAP particles and the treated fibers of the present invention.

Water retention value (WRV) is an indication of a fiber's ability to retain water under a given amount of pressure. Cellulose fibers that are soaked in water swell moderately, and physically retain water in the swollen fiber walls. When an aqueous fiber slurry is centrifuged, the majority of the water is removed from the fibers. However, a quantity of water is retained by the fiber even after centrifugation, and this quantity of water is expressed as a percentage based on the dry weight of the fiber. All of the fibers treated according to the present invention, have lower WRV values than corresponding untreated fibers. Consequently, all the treated fibers are stiffer than conventional fluff fibers, thus contribute to improved core permeability.

Reducing Agents

If desired, reducing agents may be applied to the treated fibers to maintain desired levels of fiber brightness, by reducing brightness reversion. Addition of acidic substances may cause browning of fibers when heated during processing of webs containing the fibers. Reducing agents counter the browning of the fibers. The reducing agent should also bond to the fibers. Preferred agents are sodium hypophosphite and sodium bisulfite, and mixtures thereof.

Fibers

A wide variety of fiber types may be treated with the polyvalent metal ion containing compound. However, the use of hydrophilic fibers is preferred. Suitable hydrophilic fibers for use in the present invention include cellulosic fibers, modified crosslinked cellulose fibers, rayon, polyester fibers, hydrophilic nylon, silk wool and the like. Suitable hydrophilic fibers can also be obtained by hydrophilizing hydrophobic fibers. Fibers may be hydrophilized by treatment with surfactants, silica, or surface oxidation, e.g. by ozone in a corona discharge. Such fibers may be derived from, for example, polyolefins such as polyethylene or polypropylene, polyacrylics, polyamides, polystyrenes, polyurethanes and the like.

For absorbent product applications, the preferred fiber is cellulose. Examples of suitable sources of cellulose fibers include softwood cellulose, hardwood cellulose, cotton, esparto grass, bagasse, hemp, flax, chemically modified cellulose and cellulose acetate. The preferred wood cellulose is bleached cellulose. The final purity of the preferred cellulose fiber of the present invention may range from at least 80% alpha to 98% alpha cellulose, although purity of greater than 95% alpha is preferred, and purity of 96.5% alpha cellulose, is most preferred. As used herein, the term "purity" is measured by the percentage of alpha cellulose present. This is a conventional measurement in the dissolving pulp industry. Methods for the production of cellulose fiber of various purities typically used in the pulp and paper industry are known in the art.

Curl is defined as a fractional shortening of the fiber due to kinks, twists and/or bends in the fiber. The percent curl of the cellulose fibers of the present invention is preferably from 25% to 80%, and is more preferably 75%. For the purpose of this disclosure, fiber curl may be measured in terms of a two dimensional field. The fiber curl is determined by viewing the fiber in a two dimensional plane, measuring the projected length of the fiber as the longest dimension of a rectangle encompassing the fiber, L (rectangle), and the actual length of the fiber L (actual), and then calculating the fiber curl factor from the following equation:

Curl Factor=$L$(actual)/$L$(rectangle)−1

A fiber curl index image analysis method is used to make this measurement and is described in U.S. Pat. No. 5,190,563. Fiber curl may be imparted by mercerization. Methods for the mercerization of cellulose typically used in the pulp and paper industry are known in the art.

The preferred water retention value (WRV) of the cellulose fibers of the present invention is less than 85%, and more preferably between 30% and 80%, and most preferably 40%. The WRV refers to the amount of water calculated on a dry fiber basis, that remains absorbed by a sample of fibers that has been soaked and then centrifuged to remove interfiber water. The amount of water a fiber can absorb is dependent upon its ability to swell on saturation. A lower number indicates internal cross-linking has taken place. U.S. Pat. No. 5,190,563 describes a method for measuring WRV.

Another source of hydrophilic fibers for use in the present invention, especially for absorbent members providing both fluid acquisition and distribution properties, is chemically stiffened cellulose fibers. As used herein, the term "chemically stiffened cellulose fibers" means cellulose fibers that have been treated to increase the stiffness of the fibers under both dry and wet aqueous conditions. In the most preferred stiffened fibers, chemical processing includes intrafiber crosslinking with crosslinking agents while such fibers are in a relatively dehydrated, defibrated (i.e., individualized), twisted, curled condition. These fibers are reported to have curl values greater than 70% and WRV values less than 60%. Fibers stiffened by crosslink bonds in individualized form are disclosed, for example U.S. Pat. No. 5,217,445 issued Jun. 8, 1993, and U.S. Pat. No. 3,224,926 issued Dec. 21, 1965.

SAPS

The term "superabsorbent polymer particle" or "SAP" particle is intended to include any particulate form of superabsorbent polymer, including irregular granules, spherical particles (beads), powder, flakes, staple fibers and other elongated particles. "SAP" refers to a normally water-soluble polymer which has been cross-linked to render it substantially water insoluble, but capable of absorbing at least ten, and preferably at least fifteen, times its weight of a physiological saline solution. Numerous examples of superabsorbers and their methods of preparation may be found for example in U.S. Pat. Nos. 4,102,340; 4,467,012; 4,950,264; 5,147,343; 5,328,935; 5,338,766; 5,372,766; 5,849,816; 5,859,077; and Re. 32, 649.

SAPs generally fall into three classes, namely starch graft copolymers, cross-linked carboxymethylcellulose derivatives and modified hydrophilic polyacrylates. Non-limiting examples of such absorbent polymers are hydrolyzed starch-acrylate graft co-polymer, saponified acrylic acid ester-vinyl co-polymer, neutralized cross-linked polyacrylic acid, cross-linked polyacrylate salt, and carboxylated cellulose. The preferred SAPs, upon absorbing fluids, form hydrogels.

Suitable SAPs yield high gel volumes or high gel strength as measured by the shear modulus of the hydrogel. Such preferred SAPs contain relatively low levels of polymeric materials that can be extracted by contact with synthetic urine (so-called "extractables"). SAPs are well known and are commercially available from several sources. One example is a starch graft polyacrylate hydrogel marketed under the name IM1000™ (Hoechst-Celanese, Portsmouth, Va.). Other commercially available superabsorbers are marketed under the trademark SANWET™ (Sanyo Kasei Kogyo Kabushiki, Japan), SUMIKA GEL™ (Sumitomo Kagaku Kabushiki Haishi, Japan), FAVOR™ (Stockhausen, Garyville, La.) and the ASAP™ series (Chemdal, Aberdeen, Miss.).

Suitable SAP particles for use in the present invention include those discussed above, and others, provided that the SAP particle provides improved permeability of an absorbent core made with the SAP and a hydrophilic fiber treated according to the present invention. Most preferred for use with the present invention are polyacrylate-based SAPs.

As used in the present invention, SAP particles of any size or shape suitable for use in an absorbent core may be employed.

Absorbent Core Structures

The treated fibers of the present invention may be used in combination with SAP particles, to form a stratum of an absorbent core, useful in forming an absorbent structure for use in manufacturing an absorbent article. The treated fibers begin to show improved core permeability in a mixture of 20% SAP and 80% fiber in an absorbent core, even better permeability is displayed in a mixture of 40% SAP and 60% fiber in an absorbent core, and further improvement in permeability is observed in a mixture of 60% to 80% SAP and 40% to 20% fiber in an absorbent core. Preferably, the treated fibers will be used to form one stratum of a multi-strata absorbent structure. Absorbent structures particularly useful in infant diapers and adult incontinence products often include at least two defined strata—an upper acquisition stratum and a lower storage stratum. Sometimes, a distribution stratum is provided between the acquisition and storage strata. Optionally, a wicking stratum is provided below the storage stratum.

Typically SAP particles are provided in the storage stratum, although such SAP particles may also, or alternatively be provided in a distribution stratum. The treated fibers or other treated substrates of the present invention may be located in any stratum, provided that upon exposure of the absorbent structure to a liquid insult, the liquid contacts the treated fiber, and then carries the polyvalent metal ion to the SAP particles. Preferably, in a multi-strata absorbent structure, the treated fiber of the present invention will be provided in the storage layer.

Absorbent Articles

The treated fibers of the present invention may be employed in any disposable absorbent article intended to absorb and contain body exudates, and which are generally placed or retained in proximity with the body of the wearer. Disposable absorbent articles include infant diapers, adult incontinence products, training pants, sanitary napkins and other feminine hygiene products.

A conventional disposable infant diaper generally includes a front waistband area, a rear waistband area and a crotch region there between. The structure of the diaper generally includes a liquid pervious topsheet, a liquid impervious backsheet, an absorbent structure, elastic members, and securing tabs. Representative disposable diaper designs may be found, for example in U.S. Pat. No. 4,935,022 and U.S. Pat. No. 5,149,335. U.S. Pat. No. 5,961,505 includes representative designs for feminine hygiene pads.

The absorbent structure incorporating the treated fibers of the present invention may be formed in place by blending individualized fibers and SAP particles and applying them to a form under applied vacuum to create an absorbent structure of desired shape. Alternatively, the absorbent structure may be formed separately as a continuous roll good, preferably using airlaid (or "dryformed") technology.

Fiber Treatment

The fibers suitable for use in absorbent structures may be treated in a variety of ways to provide the polyvalent metal ion-containing compound in close association with the fibers. A preferred method is to introduce the compound in solution with the fibers in slurry form and cause the compound to precipitate onto the surface of the fibers. Alternatively, the fibers may be sprayed with the compound in aqueous or non-aqueous solution or suspension. The fibers may be treated while in an individualized state, or in the form of a web. For example, the compound may be applied directly onto the fibers in powder or other physical form. Whatever method is used, however, it is preferred that the compound remain bound to the fibers, such that the compound is not dislodged during normal physical handling of the fiber in forming the absorbent structure and absorbent articles or use of the article, before contact of the fiber with liquid. Upon contact of the treated fibers with liquid, the applied compound should be released from the fiber to provide ions within the liquid.

Preferred Method of Treating Fibers

In a preferred embodiment, the treated fibers of the present invention are made from cellulose fiber, obtained from Buckeye Technologies Inc. (Memphis, Tenn.). The pulp is slurried, the pH is adjusted to about 4.0, and aluminum sulfate ($Al_2(SO_4)_3$) in aqueous solution is added to the slurry. The slurry is stirred and the consistency reduced. Under agitation, the pH of the slurry is increased to approximately 5.7. The fibers are then formed into a web or sheet, dried, and sprayed with a solution of citric acid at a loading of 2.5 weight % of the fibers. The web is then packaged and shipped to end users for further processing, including fiberization to form individualized fibers useful in the manufacture of absorbent products. If a reducing agent is to be applied, preferably it is applied before a drying step and following any other application steps. The reducing agent may be applied by spraying, painting or foaming.

Without intending to be bound by theory, it is believed that by this process, the soluble $Al_2(SO_4)_3$ introduced to the pulp slurry is converted to insoluble $Al(OH)_3$ as the pH is increased. The insoluble aluminum hydroxide precipitates onto the fiber. Thus, the resultant fibers are coated with $Al(OH)_3$ or contain the insoluble metal within the fiber interior. The citric acid sprayed on the web containing the fibers dries on the fibers. When the $Al(OH)_3$ treated fibers are formed into an absorbent product, the citric acid creates a locally acidic environment when the citric acid-treated fibers of the absorbent product are exposed to a liquid insult (e.g., urine). The decreased pH created by the acid environment converts the $Al(OH)_3$ to the soluble form of aluminum including a citric acid complex of this metal. In this way, aluminum ions may become available in solution to locally and temporarily inhibit the swelling of superabsorbent polymers (also present in the absorbent material) thereby minimizing or preventing gel-blocking.

In another preferred embodiment, the above procedure is followed to treat the fibers with precipitated $Al(OH)_3$, and in a subsequent step, aluminum sulfate is applied, preferably by spraying, onto the $Al(OH)_3$-treated fibers. Preferably the aluminum sulfate is applied to the web, before the web is introduced to web dryers. Application to the wet web provides better distribution of the aluminum sulfate through the web. The acidic environment provided by the aluminum sulfate is also conducive to release of soluble aluminum ions from the $Al(OH)_3$ precipitate.

A hierarchy of preferred embodiments is exemplified as follows: a two component mixture of (1) cellulosic fibers pretreated with a water soluble aluminum compound and (2) SAP particles in an absorbent core (Example 4), provides a higher level of core permeability than a comparable three component mixture of (1) cellulosic fibers and (2) a water soluble aluminum compound and (3) SAP particles in an absorbent core (Example 12), and a higher level of core permeability than a two component mixture of (1) SAP particles pretreated with a water soluble aluminum compound in an aqueous solution and (2) cellulosic fibers in an absorbent core (Example 15). These results are exemplified in the procedures set forth below.

Treatment of SAP Particles

Improved core permeability may be obtained by coating the surface of SAP particles with a polyvalent ion salt, and combining the coated SAP particle with a fiber in an absorbent structure. The particles are coated in contrast to reacting or complexing the SAP particles with a polyvalent cation salt. Coating of the SAP particle with the salt is accomplished by mixing the SAP particles with a non-aqueous solution of the polyvalent ion salt, and subsequently removing the non-aqueous solvent, leaving a coating of the salt on the surface of the SAP particle. For example, an anhydrous methanol solution of aluminum sulfate may be mixed with SAP particles at room temperature, for example Favor™ SXM 9100, the mixture dried, and the granular coated SAP particles mixed with fluff fiber in an absorbent core. The core permeability for such a structure is much higher than that obtained when an equivalent amount of polyvalent ion salt in aqueous solution is used to treat SAP particles, indicating superior core permeability with aluminum sulfate-coated particles compared to aluminum cation-complexed SAP particles. Although methanol is the preferred non-aqueous solvent, any solvent which dissolves the salt but does not swell the SAP particle, may be used. Examples include alcohols, such as ethanol, n-propanol, iso-propanol and acetone.

The following procedures are employed in the Examples set forth at the end of the specification.

Formation of Air Laid Structures

A Kamas mill (Kamas Industri AB, Sweden) is used to disintegrate pulp sheets into fluff pulp. A pad former (Buckeye Technologies, Memphis, Tenn.) is used to combine the fluff and SAP particles.

Laboratory air-laid absorbent structures are made by combining fiber and SAP particles in the laboratory to simulate the process of an absorbent core construction on a full-scale commercial line. Fiber and SAP particles are loaded into the pad former. Fiber and SAP particles are combined through air vortices and become one single structure via the applied vacuum. The air-laid structure is then die-cut to dimensions specific for performance testing. For testing purposes, the airlaid structure should have dimensions of 14"×14" at a target basis weight (0.30 $g/in^2$ or 0.22 $g/in^2$).

Measurement of Ion Content

Metal ion content, including aluminum or iron content, in pulp samples is determined by wet ashing (oxidizing) the sample with nitric and perchloric acids in a digestion apparatus. A blank is oxidized and carried through the same steps as the sample. The sample is then analyzed using an inductively coupled plasma spectrophotometer ("ICP") (e.g., a Perkin-Elmer ICP 6500). From the analysis, the ion content in the sample can be determined in parts per million. The polyvalent cation content should be between 0.25% and 5.0% by weight of fibers, preferably between 0.25% and 2.5% by weight of fibers, and more preferably between 0.4% and 1.2% by weight of fibers.

Measurement of Ion Extraction

The percentage of ions extracted from fibers in a saline solution is measured by submerging the test fibers in a saline solution that is shaken for 24 hours. During this period, ions are extracted from the fibers and into the solution. The ion concentration in the solution is measured using an ICP and compared with the ion content in the original fiber sample to determine the percentage of ion removed due to prolonged exposure to saline under agitation. The ion extraction should exceed 5%, preferably exceed 25%, more preferably exceed 50%, and most preferably exceed 90%

Measurement of Vertical Permeability

Vertical Permeability is determined using the following procedure. This procedure was adapted from the method disclosed in U.S. Pat. No. 5,562,642.

Figure 3:
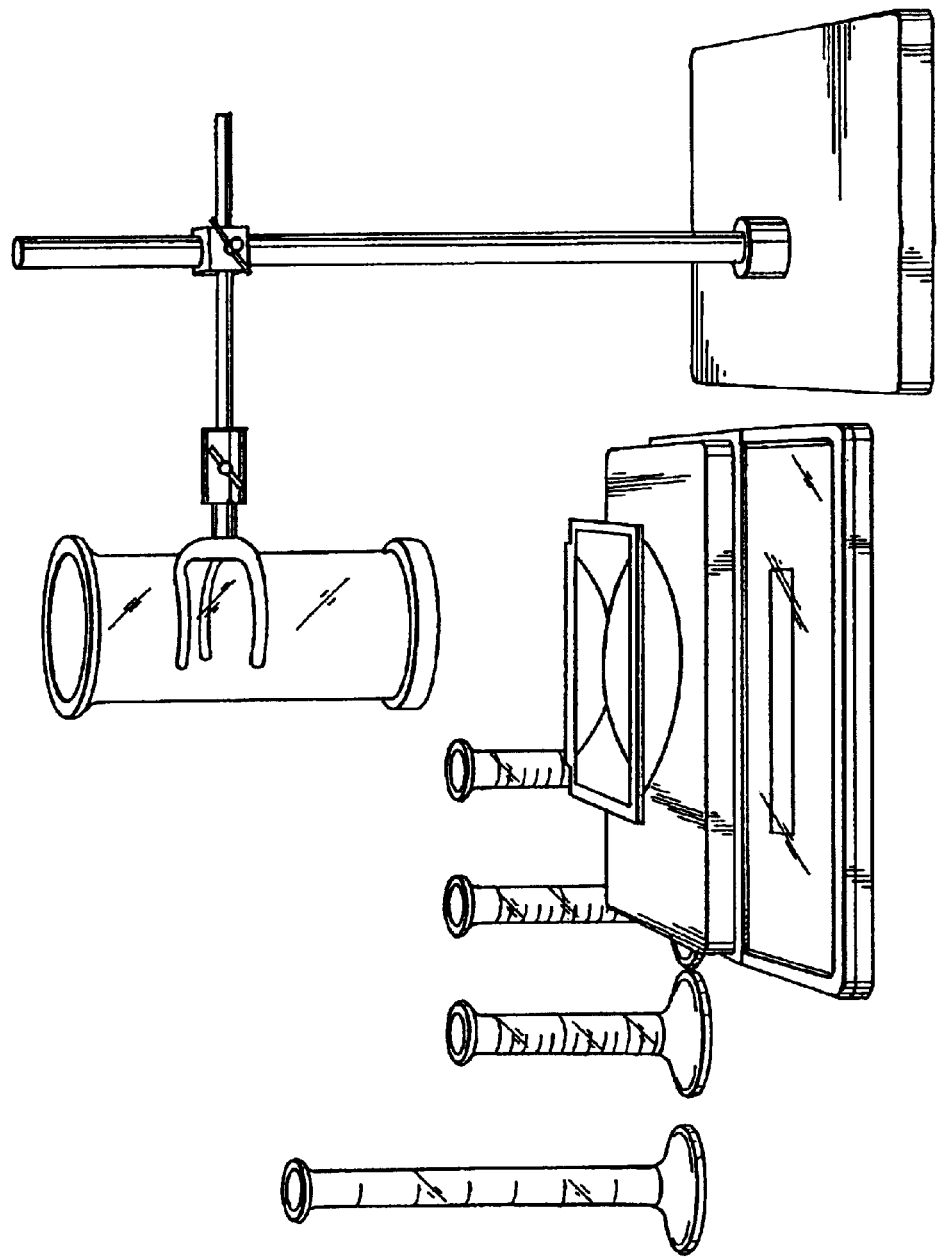
FIG. 3 is a perspective view of a vertical permeability test apparatus employed in the Examples of the present specification.

A Kamas Cell Mill (Kamas Industri AB, Sweden) apparatus is used to form disintegrated pulp sheets that in turn are used to produce fluff. A pad former (Buckeye Technologies Inc., Memphis, Tenn.) is used to combine SAP particles and fiber to prepare 14"×14" test pads. Test pads are constructed at a basis weight of 0.3 g/in$^2$ and pressed to a density of 0.15 g/cc. Samples are die-cut to 2¼" diameter circles and conditioned before testing. The circles are dried in a forced air oven, then placed in a dessicator until the permeability test is run. The sample is then positioned into a vertical cylinder that contains a base (sample platform) constructed from wire mesh. See FIG. 3 for an illustration of the vertical permeability test apparatus. The vertical cylinder has an inside diameter of 2¼". A weight placed onto the sample supplies about 0.3 lb/in$^2$ of pressure perpendicular to the sample. The sample is saturated in fluid (0.9% saline) for one hour. After one hour, the vertical cylinder containing the sample is secured over (but not in contact with) a weighing balance. The sample is initially insulted with 50 ml of 0.9% saline via a ⅜" hole centered in the weight. A 25-ml insult is added for every 25 grams of fluid that transferred to the balance until the balance reads 100 grams. Fluid transferred by the sample is measured per unit of time to quantify the permeability for a given sample. Absorption capacity for the samples is also recorded.

Measurement of Inclined Permeability

Figure 1:
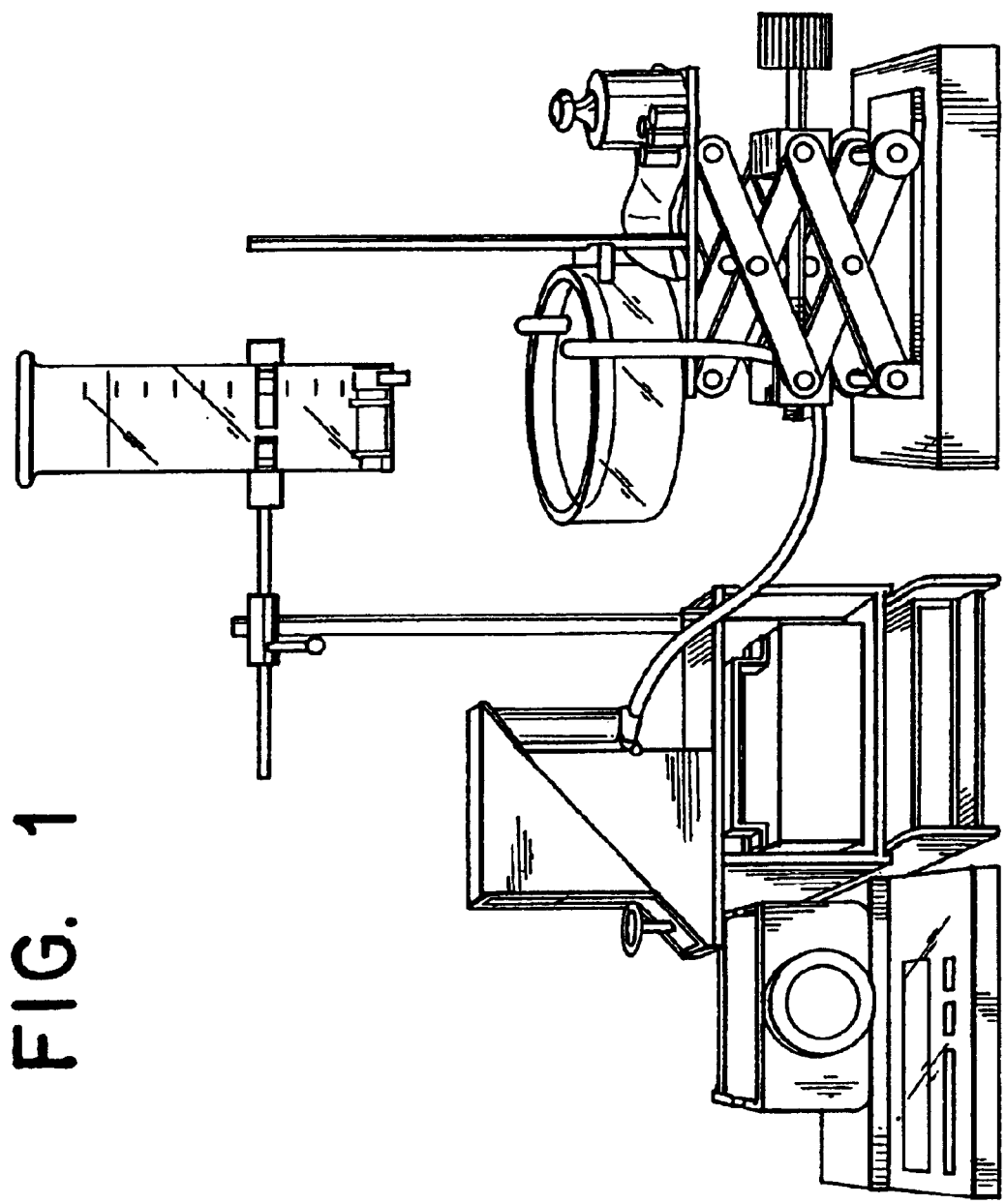
FIG. 1 is a perspective view of an inclined permeability test apparatus employed in the Examples of the present specification.
Figure 2:
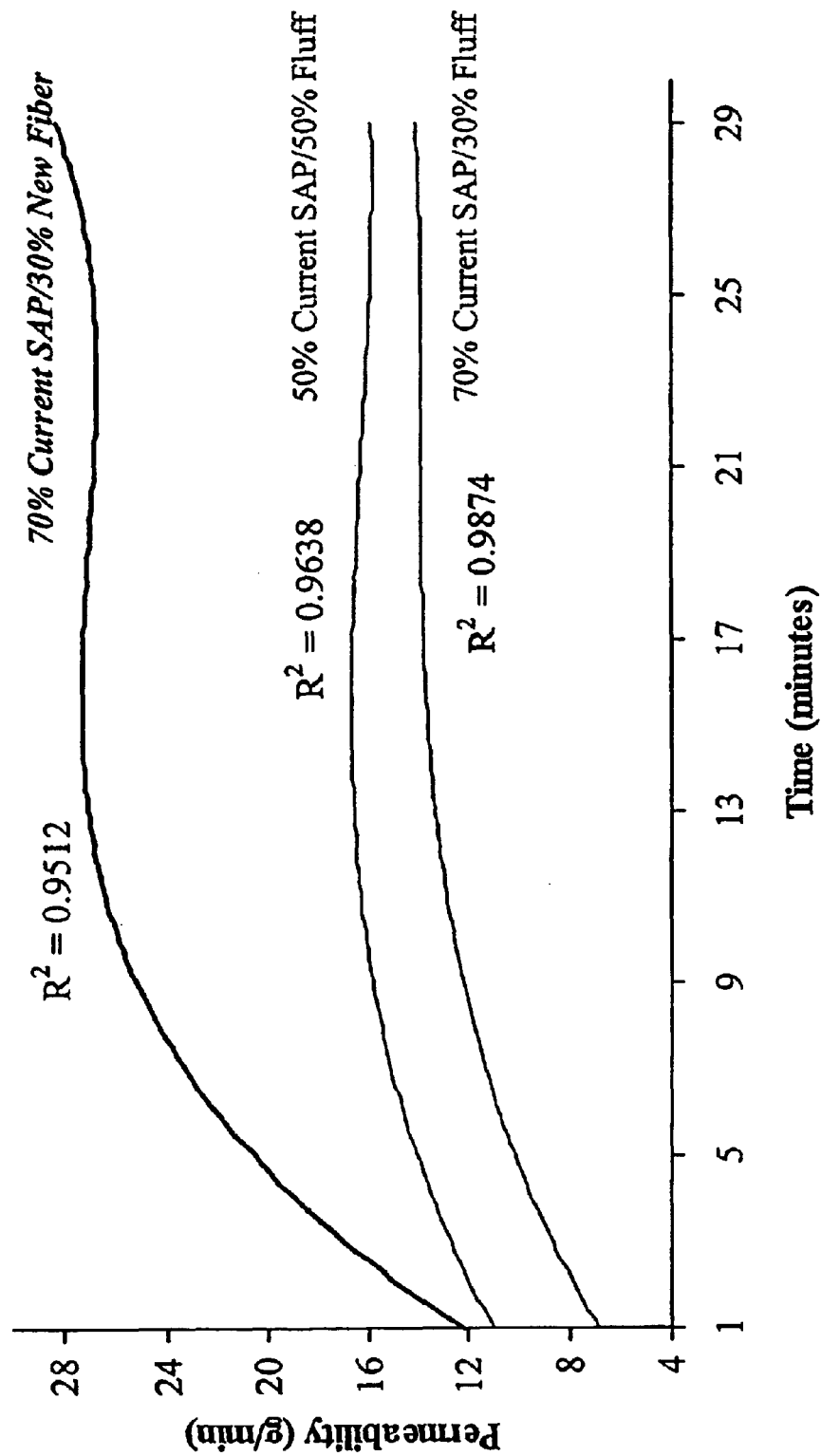
FIG. 2 is a graph illustrating the inclined permeability of absorbent structures of the present invention compared with conventional structures.

The following procedure is used to measure inclined permeability. This procedure was adapted from the procedure disclosed in U.S. Pat. No. 5,147,343. A Kamas Cell Mill (Kamas Industri AB, Sweden) apparatus is used to form disintegrated pulp sheets that in turn are used to produce fluff. A pad former was used to combine SAP particles and fibers to prepare 14"×14" test pads. Test pads are constructed at a basis weight of 0.22 g/in$^2$ and pressed to a density of 0.15 g/cc. Permeability samples are die-cut to eleven square inches and conditioned before testing. Refer to FIG. 1 for an illustration of the inclined permeability test apparatus used in the procedure. Permeability samples are placed on a Teflon coated block inclined at a 45-degree angle. Attached to this block is a fluid head box connected by ¼" tubing to a vertically adjustable fluid reservoir. The front edge of the sample pad is centered onto and secured to the head box. The head box is designed with three 3/16" diameter holes that are spaced 9/16" apart. A top block coated with Teflon, with a congruent 45-degree angle, is placed on top of the sample pad. Lubricated pegs are inserted into the bottom block (sample platform) at a 60-degree angle to prevent the top block from slipping while allowing for uniform sample expansion after saturation. A 724.4 g weight, along with the weight of the top block supplies about 0.3 lbs/in$^2$ of pressure perpendicular to the sample. The fluid (0.9% saline) level is adjusted to produce and maintain an inverted meniscus. Once saturation occurs, the sample pad acts as a siphon by transferring fluid to a tared receiving container atop a balance located below the end of the sample. Liquid transferred by the sample is measured per unit time to establish a flow rate. Permeability for a given sample is quantified after the flow rate reaches equilibrium. For example, FIG. 2 shows the incline permeability at various time intervals for 50% SAP and 50% cellulose fiber mixtures, and 70% SAP and 30% cellulose fiber mixtures. The figure also shows the increased permeability produced by the invention fiber in a mixture with SAP (Example 3).

Calculation of Permeability Factor

The permeability factor is determined by summing the permeability in gm/min from the vertical permeability and the inclined permeability. The sum is taken as follows:

$$\text{Perm Factor} = (\text{vertical}^2 + \text{inclined}^2)^{1/2}$$

where "vertical" permeability and "inclined" permeability are express as gm/min. The factor is reported as a dimensionless number although the actual dimensions are gm/min.

Measurement of Horizontal Wicking (Core Utilization)

Horizontal wicking samples of about 4"×14" are placed onto a level platform with bordering grooves to capture "runoff" fluid (0.9% saline). Both laboratory test cores or manufactured diaper cores may be used. For laboratory cores, an acquisition-distribution layer (ADL) from a commercial diaper cut to 3"×7" is placed on top of the sample where fluid is introduced. Then a second board is placed on top of the sample and ADL. The top board contained an insult reservoir with a 1½" inside diameter. The insult region, relative to the sample, was 5" centered from the front end or end closest to the insult reservoir. Two 10 lb. weights placed on the top board along with the weight of the top board supplied about 0.40 lbs/in$^2$ of pressure perpendicular to the sample. Three 100 ml insults were introduced to the sample in twenty-minute intervals. After one hour, the sample was sectioned and weighed to determine the distance that liquid was transported away form the insult region. Horizontal wicking was quantified by the sum of the last three inches, on a gram of fluid per gram of core sample basis.

The following examples are intended to illustrate the invention without limiting its scope.

COMPARATIVE EXAMPLE 1

A slurry of bleached southern softwood Kraft (BSSK) fibers from Buckeye Technologies consisting of 4.5 parts fiber/100 parts slurry was diluted with sufficient water to provide 0.9 parts fiber/100 parts slurry and adjusted to a pH of 5.5. The resultant slurry was continuously dewatered on a sheeting machine where a sheet was formed at rush/drag ratio of 1.0, couched, then pressed and densified through three stages of pressing to 48 parts fiber/100 parts slurry. The sheet was dried using conventional drum dryers to 93.5 percent solids. The sheet was reeled on a continuous roll.

Sheets from the roll were defiberized in a Kamas mill. An ion extraction test was performed on the fibers as described above. The ionic extraction of the fiber was measured at 0%. Vertical and inclined permeability tests were performed as described above using test cores that were a mixture of 70% by weight of SAP particles and 30% by weight of fibers. The permeability factor was then calculated. When FAVOR™ SXM 70 SAP (obtained from Stockhausen, Inc.) was used, a permeability factor of 16 was obtained.

COMPARATIVE EXAMPLE 2

Comparative Example 1 was repeated, except that SAP FAVOR™ SXM 9100 was used instead of FAVOR™ SXM 70. The permeability factor obtained was 141.

EXAMPLE 1

Cellulose fibers were treated as follows. A total of 9.36 parts hydrated aluminum sulfate ($Al_2(SO_4)_3*14H_2O$) from General Chemical Corporation, per 100 parts bleached southern softwood Kraft (BSSK) fibers from Buckeye Technologies were added to a slurry consisting 4.5 parts fiber/100 parts slurry. The slurry had a pH of 3.2. After 25 minutes of mixing 3.0 parts sodium hydroxide/100 parts fiber were added along with sufficient water to provide 0.9 parts fiber/100 parts slurry at a pH of 5.7. The temperature was adjusted to 60° C. The resultant slurry was continuously dewatered on a sheeting machine where the sheet was formed at 1.0 rush/drag ratio, couched, then pressed and densified using three stages of pressing to 48 parts fiber/100 parts total. The sheet was dried using conventional drum dryers to 93.5 percent solids. While continuously reeling, a spray of 50% citric acid solution was applied to one surface of the sheet at a loading of 2.5 parts per 100 parts of fiber. The reeled sheet was then sized into individual rolls.

The sheet was defiberized in a Kamas mill, and the ionic extraction test described above was performed. The fiber was found to have an ionic extraction of 34% and an aluminum content of approximately 7,500 ppm. Vertical and inclined permeability tests were performed on test cores using a mixture of 70% by weight of SAP particles and 30% by weight of fibers. The permeability factor using FAVOR™ SXM 70 SAP was 31.

EXAMPLE 2

Example 1 was repeated except that the SAP used was FAVOR™ SXM 9100. The permeability factor obtained was 177.

EXAMPLE 3

A slurry of bleached southern softwood Kraft (BSSK) fibers from Buckeye Technologies consisting of 4.5 parts fiber/100 parts slurry was diluted with sufficient water to provide 0.9 parts fiber/100 parts slurry and adjusted to a pH of 5.5. The resultant slurry was continuously dewatered on a sheeting machine and a sheet was formed at a rush/drag ratio of 1.0, couched, then pressed and densified through three stages of pressing to 48 parts fiber/100 parts slurry. The sheet was dried using conventional drum dryers to 93.5 percent solids. The sheet was then reeled. During reeling, 6.1 parts of hydrated aluminum sulfate ($Al_2(SO_4)_3*14H_2O$, 50% aqueous solution) is applied by spraying per 100 parts fiber. The fiber was reeled on a continuous roll. The resultant reel was sized into individual rolls. The sheets were defiberized in a Kamas mill and the ionic extraction measured, and determined to be 86%. The aluminum content of the fibers was 5,500 ppm. Permeability tests were conducted as described above using test cores that were a mixture of 70% by weight SAP and 30% by weight fibers. The permeability factor using FAVOR™ SXM 70 SAP was 44.

EXAMPLE 4

Example 3 was repeated except that the aluminum content of the fibers was 5445 ppm, and the SAP used was FAVOR™ SXM 9100. The permeability factor obtained was 212. The ion extraction was 86%.

EXAMPLE 5

12.1 g of ferric nitrate ($Fe(NO_3)_3$) (Fisher Chemical Co.) per 152 g bleached southern softwood Kraft (BSSK) fibers from Buckeye Technologies were added to a slurry of 4.5 parts fiber/100 parts slurry. The slurry had a pH of 2.76. After mixing and dilution to 0.9 parts fiber/100 parts slurry, 27.1 ml of 10% sodium hydroxide were added to provide a pH of 5.7. The resultant slurry was dewatered on a dynamic handsheet former (Formette Dynamique Brevet, Centre Technique de L'Industrie, Ateliers de Construction Allimand, Appareil No. 48) and was pressed to 48 parts fiber/100 parts total. The sheet was dried to 93.5 percent solids. After drying, 2.5 parts of 50% citric acid solution per 100 parts of fiber were applied to the sheet.

The sample sheet was defiberized in a Kamas mill as described above. Permeability was determined on test cores formed as described above, that were a mixture of FAVOR™ SXM 9100, at 70% by weight and fiber 30% by weight. The permeability factor was calculated to be 178.

EXAMPLE 6

9.36 parts hydrated aluminum sulfate ($Al_2(SO_4)_3*14H_2O$) per 100 parts bleached southern softwood Kraft (BSSK) fibers from Buckeye Technologies were added to a slurry consisting of 4.5 parts fiber/100 parts slurry. After addition of the aluminum sulfate, the slurry had a pH of 3.2. After 25 minutes of mixing, 3.0 parts sodium hydroxide/100 parts fiber were added along with sufficient water to provide 0.9 parts fiber/100 parts slurry at a pH of 5.7 and temperature of 60° C. The resultant slurry was continuously dewatered on a sheeting machine and a sheet formed at a 1.0 rush/drag ratio, couched, then pressed and densified using three stages of pressing to 48 parts fiber/100 parts total. The sheet was dried to 93.5 percent solids. To this sheet sample was applied three parts 1,2,3,4-butanetetracarboxylic acid (BTCA) from Aldrich Chemical Company per 100 parts of fiber by spraying a solution.

The sheet was defiberized in a Kamas mill and the fiber was determined to have an ionic extraction of 12.4%. All permeability factor testing was performed using pads made with 70% by weight of FAVOR™ SXM 70 SAP and 30% weight of fiber. The permeability factor was determined to be 38.

EXAMPLE 7

9.36 parts hydrated aluminum sulfate ($Al_2(SO_4)_3*14H_2O$) per 100 parts bleached southern softwood Kraft (BSSK) fibers from Buckeye Technologies were added to a slurry consisting of 4.5 parts fiber/100 parts slurry. After addition of the aluminum sulfate, the slurry had a pH of 3.2. After 25 minutes of mixing, 3.0 parts sodium hydroxide/100 parts fiber were added along with sufficient water to provide 0.9 parts fiber/100 parts slurry at a pH of 5.7 and temperature of 60° C. The resultant slurry was continuously dewatered on a sheeting machine and a sheet formed at a 1.0 rush/drag ratio, couched, then pressed and densified using three stages of pressing to 48 parts fiber/100 parts total. The sheet was dried to 93.5 percent solids. To this sheet sample was applied one part para-toluenesulfonic acid (PTSA) from Aldrich Chemical Company by spraying per 100 parts of fiber.

The sheet was defiberized in a Kamas mill and the fiber was determined to have an ionic extraction of 13.4%. All permeability factor testing was performed using test cores made with 70% by weight of FAVOR™ SXM 70 SAP and 30% by weight of fiber. The permeability factor was determined to be 32.

EXAMPLE 8

High porosity commercial fiber (HPZ) was obtained from Buckeye Technologies Inc. in sheet form. The fibers had a WRV of 78.7, a curl of 51% and a 96.5 % alpha cellulose content. A total of 7.7 parts of hydrated aluminum sulfate octadecahydrate (Aldrich Chemical Company) per 100 parts fiber were applied to the sheeted material by spraying.

Ion extraction was measured for the fiber as 100%. Permeability was measured after preparing a test pad that was 30% by weight of fibers and 70% by weight of FAVOR™ SXM 9100 SAP. The permeability factor was 241.

EXAMPLE 9

High purity commercial cotton fiber (GR702) was obtained from Buckeye Technologies Inc. in sheet form. A total of 7.7 parts of aluminum sulfate octadecahydrate per 100 parts fiber were applied to the sheeted material by spraying. Ion extraction was measured for the fiber as 99.0%. Permeability was measured after preparing a pad that was 30% by weight of fibers and 70% by weight of FAVOR™ SXM 9100 SAP. The permeability factor was 219.

EXAMPLE 10

Fibers were prepared as disclosed in U.S. Pat. No. 5,190,563 by applying 4.7% citric acid and 1.6% sodium hypophosphite to a Southern Softwood Kraft pulp sheet. After individualizing and curing at 340° F. for 7.5 minutes, the pulp had a WRV of 44 and a curl of about 75%. The individualized fibers were treated by spraying 3.42 parts of hydrated aluminum sulfate ($Al_2(SO_4)_3*14H_2O$) per 100 parts fiber were added to the fibers and the fibers allowed to dry. The ionic extraction for the fibers was measured at 49.8%. The aluminum content of the fibers was measured at 10,869 ppm. Test pads were made with 30% by weight of the treated fibers and 70% by weight FAVOR™ SXM 9100 SAP and the permeability factor measured. The factor was found to be 231.

EXAMPLE 11

A sheet of synthetic hydrophilic non-woven material from BBA corporation, product number H018B7W, was selected and treated with 1.03 grams of aluminum sulfate octadecahydrate per square foot of material by spraying and allowed to dry. Test pads were made from 30% by weight bleached southern softwood Kraft (BSSK) fibers from Buckeye Technologies and 70% by weight FAVOR™ SXM 9100 SAP, with the treated non-woven material as a topsheet, and the permeability factor measured. The permeability factor was 191.

EXAMPLE 12

An absorbent core of improved permeability was prepared by adding 2.4 parts of aluminum sulfate octadecahydrate (51.3% aluminum sulfate) in powder form to 100 parts of a 30% by weight fiber and 70% by weight SAP core as described in the method for producing cores. The permeability factor with FAVOR™ SXM 9100 at 70% SAP was 207.

EXAMPLE 13

A slurry of bleached southern softwood Kraft (BSSK) fibers Buckeye Technologies consisting of 4.5 parts fiber/100 parts slurry was diluted with sufficient water to provide 0.9 parts fiber/100 parts slurry and adjusted to a pH of 5.5. The resultant slurry was continuously dewatered on a sheeting machine where the sheet was formed at a rush/drag ratio of 1.0, couched, then treated by spraying with 12.35 parts of hydrated aluminum sulfate and 3.17 parts of sodium hypophosphite per one hundred parts of fiber, then pressed and densified through three stages of pressing to 48 parts fiber/100 parts slurry. The sheet was dried using conventional drum dryers to 93.5 percent solids. The fiber was reeled on a continuous roll. The resultant reel was sized into individual rolls.

The sheets were defiberized in a Kamas mill and the ionic extraction of the fiber was measured at 95%. The permeability factor was determined to be 216, using at test core that was 30% by weight fiber and 70% by weight FAVOR™ SXM 9100.

EXAMPLE 14

A total of 9.36 parts of hydrated aluminum sulfate ($Al_2(SO_4)_3*14H_2O$) per 100 parts of bleached southern softwood Kraft (BSSK) fibers from Buckeye Technologies were added to a slurry consisting of 4.5 parts fiber/100 parts slurry. The slurry had a pH of 3.2. After 25 minutes of mixing, 3.0 parts of sodium hydroxide per 100 parts of fiber were added with sufficient water to provide 0.9 parts fiber per 100 parts slurry at a pH of 5.7 and at a temperature of 60° C. The resultant slurry was continuously dewatered on a sheeting machine where the sheet was formed at a rush/drag ratio of 1.0, couched, then treated by spraying with 12.35 parts of hydrated aluminum sulfate and 3.17 parts of sodium hypophosphite per one hundred parts of fiber, then pressed and densified through three stages of pressing to 48 parts fiber/100 parts slurry. The sheet was dried using conventional drum dryers to 93.5 percent solids. The fiber was reeled on a continuous roll. The resultant reel was sized into individual rolls.

The sheets were defiberized in a Kamas mill and the ionic extraction of the fiber was measured at 38.2% and the aluminum content was 9475 ppm. The permeability factor was determined to be 213, using a test core that was 30% by weight fiber and 70% by weight FAVOR™ SXM 9100.

EXAMPLE 15

An absorbent core was prepared by combining three parts of defiberized fluff fiber by weight with seven parts by weight of pretreated FAVOR™ SXM 9100 SAP. The FAVOR™ SXM 9100 SAP had been pretreated with aqueous aluminum sulfate octadecahydrate at ratio of 3.7 parts of dry aluminum sulfate octadecahydrate to 100 parts of SAP, dried at 125° C. for 3 hours, crushed and sieved to the same particle size as the untreated SAP. The permeability factor for this core was determined to be 187.

EXAMPLE 16

An absorbent core was prepared by combining three parts of defiberized fluff fiber by weight with seven parts by weight of pretreated FAVOR™ SXM 9100 SAP. The FAVOR™ SXM 9100 SAP had been pretreated with a methanol solution of aluminum sulfate octadecahydrate at a ratio of 3.7 parts of dry aluminum sulfate octadecahydrate to 100 parts of SAP, air dried in an exhaust hood to remove visible liquid, and oven dried at 40° C. for two hours. The permeability factor for this core was determined to be 268.

What is claimed is:

1. Fibers bound with a polyvalent cation-containing compound, the fibers exhibiting an ion extraction factor of at least 5%, and further comprising an ionizable acid bound to at least one fiber.

2. The fibers of claim 1 wherein the acid is present in an amount of between 0.5% and 10%, by weight of the fiber.

3. The fibers of claim 1 wherein the acid is an organic acid having at least two carboxylic acid groups.

4. The fibers of claim 3 wherein the acid is a selected from the group consisting of C2 to C12 organic acids.

5. The fibers of claim 3 wherein the acid is citric acid.

6. The fibers of claim 5 wherein the citric acid is present in an amount of between 0.5% and 3%, by weight of the fiber.

7. The fibers of claim 1 wherein the acid is a polymeric carboxylic acid.

8. The fibers of claim 1 wherein the acid is a sulfonic acid.

9. The fibers of claim 1 wherein the acid is a polymeric sulfonic acid.

10. The fibers of claim 1 wherein the acid is oxalic acid.

11. The fibers of claim 1 wherein the acid is selected from the group consisting of citric acid, butanetetracarboxylic acid, aspartic acid, malic acid, maleic acid, tartaric acid, para-toulenesulfonic acid, and mixtures thereof.

12. Fibers bound with a polyvalent cation-containing compound, the fibers exhibiting an ion extraction factor of at least 5%, and further comprising a reducing agent bound to the fiber.

13. The fibers of claim 12 wherein the reducing agent is selected from the group consisting of sodium hypophosphite, sodium bisulfite and mixtures thereof.

* * * * *